(12) United States Patent
Schmidt

(10) Patent No.: US 6,833,950 B2
(45) Date of Patent: Dec. 21, 2004

(54) MICROSURGICAL MICROSCOPE SYSTEM

(75) Inventor: Martin Schmidt, Bad Schwartau (DE)

(73) Assignee: Moller-Wedel GmbH, Wedel (DE)

( * ) Notice: Subject to any disclaimer, the term of this patent is extended or adjusted under 35 U.S.C. 154(b) by 0 days.

(21) Appl. No.: 10/364,954

(22) Filed: Feb. 12, 2003

(65) Prior Publication Data
US 2003/0151805 A1 Aug. 14, 2003

(30) Foreign Application Priority Data
Feb. 13, 2002 (EP) .............................................. 02003355

(51) Int. Cl.[7] .............................................. G02B 21/00
(52) U.S. Cl. ................................... 359/384; 248/281.11
(58) Field of Search ................................ 359/368, 382, 359/389; 248/123.11, 280.11, 281.11, 585

(56) References Cited

U.S. PATENT DOCUMENTS

| 5,061,018 A | | 10/1991 | Pederson et al. |
| 5,651,718 A | * | 7/1997 | Nakamura ............... 248/123.2 |
| 5,812,301 A | * | 9/1998 | Nakamura .................. 359/384 |
| 6,050,530 A | * | 4/2000 | Nakamura ............... 248/123.2 |

FOREIGN PATENT DOCUMENTS

| EP | 0 628 290 A | 12/1994 |
| WO | WO 98 53244 | 11/1998 |

* cited by examiner

Primary Examiner—Mark A. Robinson
(74) Attorney, Agent, or Firm—Alix, Yale & Ristas, LLP

(57) ABSTRACT

The microsurgical microscope system with a stand and with a parallelogram linkage is characterized in that a bar, which connects two substantially horizontal bars and to which the microscope is connected, also has a receiving device connected to it for accessory parts of the microscope and/or additional weights.

15 Claims, 5 Drawing Sheets

MICROSURGICAL MICROSCOPE SYSTEM

BACKGROUND OF THE INVENTION

The invention relates to a microsurgical microscope system with a stand and with a microscope arranged thereon, in which system the stand has a base part and a substantially horizontal parallelogram linkage with two substantially horizontal bars and first and second further bars connecting the horizontal bars, of which the first further bar is connected to a mounting device for the microscope.

For operations on fine biological structures, in particular for neurosurgical operations on the brain and spinal cord, but also in the ENT field, operating microscopes are used which are arranged on easily movable stands near the operating site.

Depending on the type of operation, operating microscopes and stands of different size and design are used. In neurosurgery, systems have proven particularly useful in which the stand has weights which, in the manner of a balance, compensate the weight of the operating microscope. However, since the microscope has to be moved in the three spatial directions, the stand must have at least three axes of movement. While one axis can be arranged vertically and for this reason no weight compensation has to take place around this axis, it is necessary to effect the balance about two axes by changing the weights or moving the weights.

A great many examples of such stands can be found in the patent literature. In particular, U.S. Pat. No. 5,528,417 describes a system in which the microscope weight is compensated by a counterweight which is moved along a curve depending on the weight of the microscope. In this system, the holder for the microscope is additionally held horizontally by connecting bars, so that the microscope is always suspended vertically under the holder.

Depending on the operation, different additional parts are needed on the operating microscope, and these alter the weight of the operating microscope. For this reason, the system has to be balanced again after the microscope has been re-equipped.

However, regularly required weight compensation has disadvantages. For compensating the shift in weight, the range of compensation is limited and has to be widened by arranging additional weights on the stand, if necessary. In the case of automatic balancing, a high level of electromechanical expenditure is necessary, which considerably increases the costs of a system. If it is forgotten to carry out the balancing procedure, the result is inconvenience for the surgeon or even a danger to the patient through uncontrolled movements of the microscope.

For these reasons, the microscopes are equipped with all possible accessory parts, even if these are not required for an operation. In this way it is possible to dispense with a balancing procedure before the operation and thus avoid the associated risk of imbalance. The disadvantage, however, is that the microscope is made large and unwieldy by the many accessory parts and greatly obstructs the view of the operating site.

The invention starts out from a microscope system of the type mentioned in the introduction (U.S. Pat. No. 5,528, 417). The object of the invention is to make available a microscope system in which accessory parts can be arranged on and removed from the microscope without the need for renewed balancing.

SUMMARY OF THE INVENTION

The solution according to the invention lies in the fact that the first further bar also has a receiving device connected to it for accessory parts of the microscope and/or additional weights.

The invention makes use of the knowledge that in this microscope system the balancing does not change if the weight acting on the parallelogram linkage does not change. This weight does not change, however, if parts of the microscope, which is connected to the first further bar of the parallelogram linkage, are removed and are arranged in or on the receiving device for the accessory parts, which is likewise connected to the first further bar of the parallelogram linkage. The fact that the distance of these objects from other parts of the stand or any of the hinges of the parallelogram linkage changes, which change would cause different rotational moments, surprisingly is not important here. This is due to the fact that, even upon swiveling of the parallelogram linkage, the orientation of the first further bar of the parallelogram linkage and of the microscope and accessory parts arranged thereon does not change.

Accessory parts which are not required at a given time do not therefore impede the work with the microscope because they can be removed from the microscope and can be arranged in or on the receiving device for accessory parts, where they no longer obstruct the work with the microscope. The corresponding parts do not have to be carried through the operating theatre and in particular taken to other rooms, which would entail the risk of these parts being damaged, mislaid or contaminated. A new balancing procedure after exchange of an accessory part is not necessary. Instead, the balancing procedure can be carried out once for a defined microscope and for a defined set of accessory parts. No automatic balancing devices of any kind are required any longer. In this way, the stand as a whole can be made lighter, smaller and less expensive.

In some circumstances, the accessory parts for the microscope take up a relatively large amount of space, so that it can be difficult to accommodate them at the end of the parallelogram linkage in the receiving device. In this case, a receiving device for accessory parts of the microscope and for additional weights can be provided on the base part. For each accessory part in this case, an equally heavy additional weight is provided which, if it is made of solid metal for example, obviously takes up a much smaller volume than the accessory part. If the relatively large-volume accessory part is not needed, it can be accommodated in the receiving device on the base part, where there is sufficient space. In its place, the substantially smaller additional weight is then arranged in the receiving device at the outer end of the parallelogram linkage near the microscope.

The invention can be used on all stands in which the microscope is arranged on a substantially horizontal parallelogram linkage. "Substantially horizontal" is intended to signify only that the stand part in question is not a substantially vertical stand part, which is more or less vertical above a foot part, for example, but instead an arm which extends to the side of the foot part or base part and at whose end the microscope is arranged. The parallelogram arm could for example be arranged on a vertical column or on a horizontal double-hinge arm which permits coverage of the XY horizontal surface.

A particularly advantageous microscope system in which the parallelogram linkage forms a first parallelogram linkage is characterized in that the stand also has:

a second substantially vertical parallelogram linkage with two substantially vertical bars and two substantially horizontal bars, of which one of the substantially vertical bars is mounted on the base part so as to be able to pivot about a pivot axle, a third substantially vertical parallelogram linkage whose first lower hinge on the pivot axle of one of the substantially vertical bars of the second parallelogram linkage is connected to the base part, and whose second lower hinge is likewise connected to the base part and is connected via its upper bar to the first parallelogram linkage, where a substantially horizontal bar of the first parallelogram linkage is a continuation of the upper substantially horizontal bar of the second parallelogram linkage, where the second lower hinge of the third parallelogram linkage is arranged higher than the first, the connection line between first and second hinge forms with the horizontal an angle of approximately 30° to 60°, and the upper bar of the third parallelogram linkage forms the second further bar of the first parallelogram linkage.

In the already known microscope system, the first parallelogram linkage and the third parallelogram linkage are connected via a lever with two branches which between them enclose an angle of 90°. The lower branch is always held horizontal, and the upper branch is always held vertical. This provides a very great range of pivoting for the first parallelogram linkage and consequently for the microscope arranged thereon. However, in the normal position, when the first parallelogram forms a rectangle, said first parallelogram is horizontal, with the result that the operating surgeon can strike his head on it. For this reason, in the prior art, it is necessary for the substantially horizontal bars to be arranged high up or for them to have a curvature away from the operating site. In the microscope system according to the invention, this is not necessary if provision is made that the second lower hinge of the third parallelogram linkage is arranged higher than the first, and that the connection line between the first and second hinges forms with the horizontal an angle of approximately 30° to 60°, and that the upper bar of the third parallelogram linkage forms the second further bar of the first parallelogram linkage.

In this case, that bar of the first parallelogram linkage which is situated near the second and third parallelogram linkages is not vertical, but instead at an angle of approximately 30° to 60°, preferably 45°, so that in this normal position the first parallelogram linkage is directed obliquely upwards and the operating surgeon has room to stand below it.

After all the necessary accessory parts and the corresponding additional weights are arranged in the receiving device on the first parallelogram linkage or on the microscope, this microscope system can be equilibrated. This is expediently done by weights which can be arranged on the parallelogram linkages, in particular on the second parallelogram linkage. This balancing can be carried out once by a technician or by a theatre nurse for a given system, and it can be retained as long as the additional devices for the microscope are not replaced by others.

Electrically or pneumatically releasable brakes are expediently arranged on hinges and/or the pivot axle. These brakes are released only if the stand is to be adjusted, that is to say if the microscope is to be moved to another position.

A particularly expedient configuration is characterized in that the bars of the parallelogram linkages are pipes which are held in bushings which form parts of the hinges and/or of the pivot axle. The hinge axles and/or the pivot axle can be arranged in the bushings outside the longitudinal axis of the pipes. To create more space for the operating surgeon, at least one bar of the parallelogram linkage can be curved in the direction away from the operating site.

The base part will expediently rest on the floor and can be provided in a manner known per se with lockable castors. However, it could also be arranged, for example, on the wall or on the ceiling of the operating theatre. The base part expediently has a foot part and a column which is pivotable about a vertical axle and on which the further parts of the stand are then arranged.

However, the main feature of the invention is that, when the stand is swiveled, the angle at which the microscope and the receiving device for the accessory parts are oriented does not change. If the total weight of the microscope and of the accessory parts which are arranged on the microscope or on/in the receiving device does not change, the balance is maintained.

BRIEF DESCRIPTION OF THE DRAWING

The invention will be described below on the basis of advantageous embodiments and with reference to the attached drawings in which.

DETAILED DESCRIPTION OF THE PREFERRED EMBODIMENTS

Figure 1:
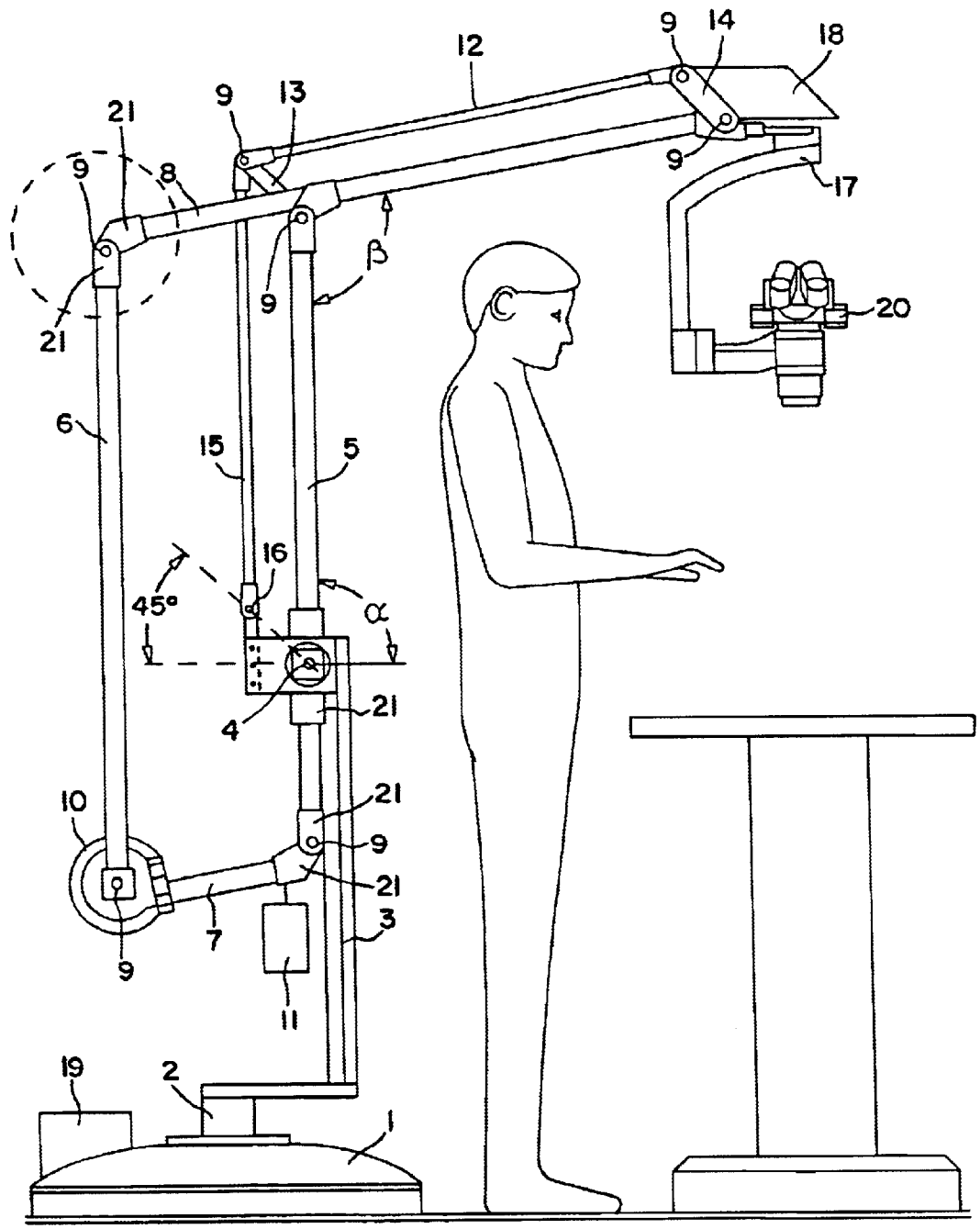
FIG. 1 shows the microscope system according to the invention in a diagrammatic view from the side.

Referring to FIG. 1, a column 3 which is pivotable about a vertical axis is arranged on a foot part 1 via a hinge 2. A parallelogram linkage, which is referred to below as the "second parallelogram linkage", is arranged on this column 3 so as to pivot about a horizontal pivot axle 4. This second parallelogram linkage has vertical bars 5, 6 and substantially horizontal bars 7, 8 which are each connected by hinges 9. Balancing weights 10 with which the stand can be equilibrated are arranged on the lower left hinge 9. The hinge connection which connects bars 6 and 7 could be an axle which is fixed to bar 7 or weight 10. To this axle bar 6 is rotatably fixed. Also the weight 10 can be fixed to bar 7. Weight 10 could e.g. be fixed to bar 7 with a screw thread connection in order that it can be changed. Instead of providing such weights 10 only at one position, it is also possible for such weights to be provided at another position, for example weights 11 on the lower bar 7, as is shown in FIG. 1. Weight 11 can, as indicated in FIG. 1, be merely suspended from bushing 21 by a wire or a bar. It also could be fixed by a screw connection to bushing 21 or bar 7. Movable weights could also be arranged on the bar 6 or 7.

The upper bar 8 of the second parallelogram linkage 5 to 9 is continued to the right and here forms part of a first parallelogram linkage which, in addition to said bar 8, has a substantially horizontal bar 12 and two further bars 13, 14. The bars 8, 12, 13, 14 are likewise connected by hinges 9 to form a parallelogram linkage. The bar 13 here forms a part of a third parallelogram linkage which, in addition to the bar 13, has a part of the bar 5 of the second parallelogram linkage, as far as the pivot axle 4, a further substantially vertical bar 15 which is mounted at 16 on the base part 1, 2, 3, and which forms the connection between pivot axle 4 and hinge 16. The connection line between pivot axle 4 and hinge 16 is in this case at said angle of approximately 30° to 60°, here in particular 45° (as shown in FIG. 1), to the horizontal, by which means the corresponding orientation of the bar 13 is fixed.

The mounting device 17 for the microscope is connected to the further bar 14 which, even upon swiveling of the parallelogram linkage, remains parallel to the bar 13 and thus does not change its orientation. A receiving device 18 for accessory parts of the microscope is also connected to this first further bar 14 of the first parallelogram linkage. This receiving device 18 can accommodate not only accessory parts (not shown in the figure) of the microscope, but also additional weights whose mass corresponds to the mass of accessory parts which, when not in use, can be accommodated in a receiving device 19 on the foot 1 of the microscope. The microscope itself is indicated at 20.

Figure 2:
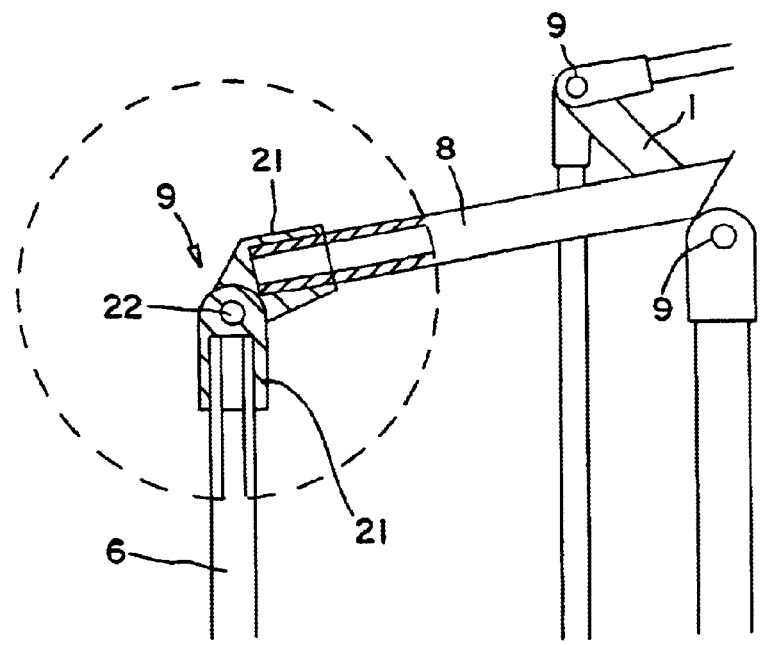
FIG. 2 is a detail of the encircled portion of FIG. 1 in cross section.

As shown in FIG. 2 which is an enlarged cross section view of the encircled portion of FIG. 1, bars 6 and 8 are hollow pipes which are held in bushings 21 which form part of the hinges 9. These hinges comprise two bushings 21 and an axle 22 which connects the two bushings in a rotational manner.

Figure 3:
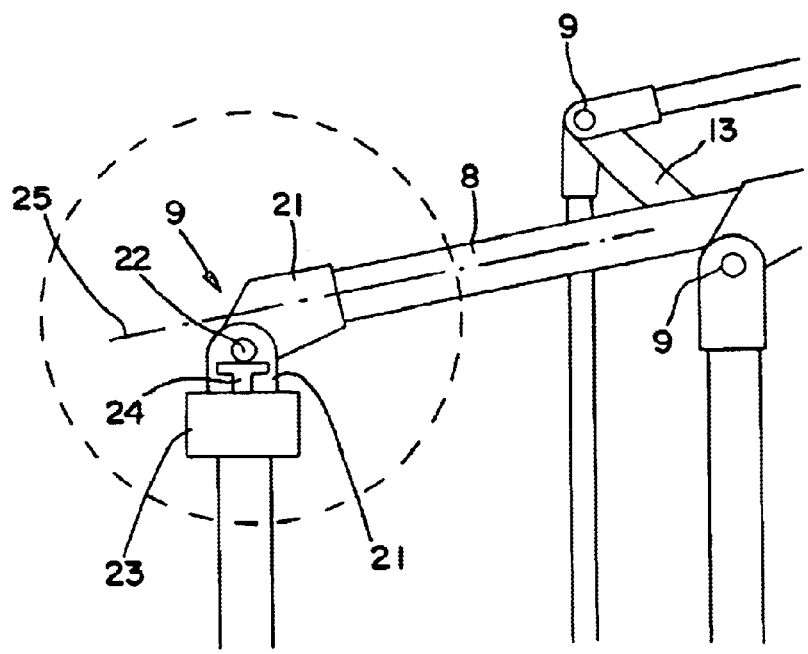
FIG. 3 is a detail of another embodiment corresponding to the encircled portion of FIG. 1.

As can be seen in FIG. 3, the relative rotation of the two bushings can be blocked by a brake which contains a solenoid or pneumatic cylinder 23 which can press a plunger 24 against axle 22 which in this case is fixed to upper bushing 21 and can rotate within lower bushing 21.

As can also be seen in FIG. 3, the axle 22 can be arranged outside the longitudinal axis 25 of the bar or pipe 8. This, of course, can be the case also for other hinge axles or pivot axles.

Figure 5:
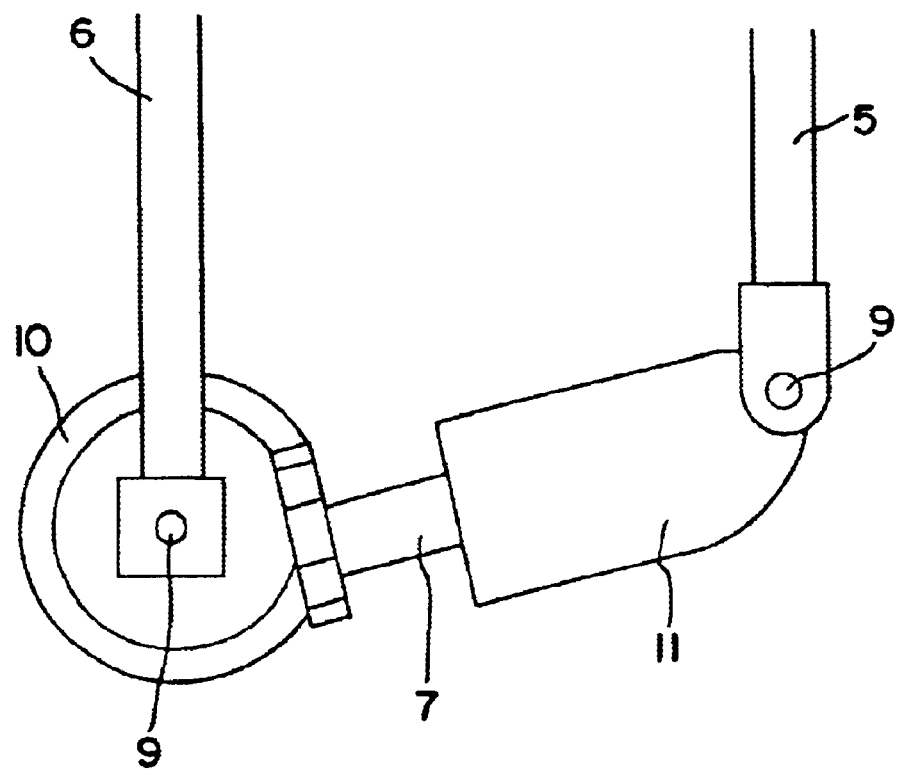
FIG. 5 is a detail of another embodiment corresponding to the lower left hand side of the parallelogram linkage of FIGS. 1 and 4.

In FIG. 5, details of another embodiment are shown in which weight 11 is integral with bar 7, this integral unit connecting the lower hinge 9 of bar 5 with weight 10.

Figure 6A:
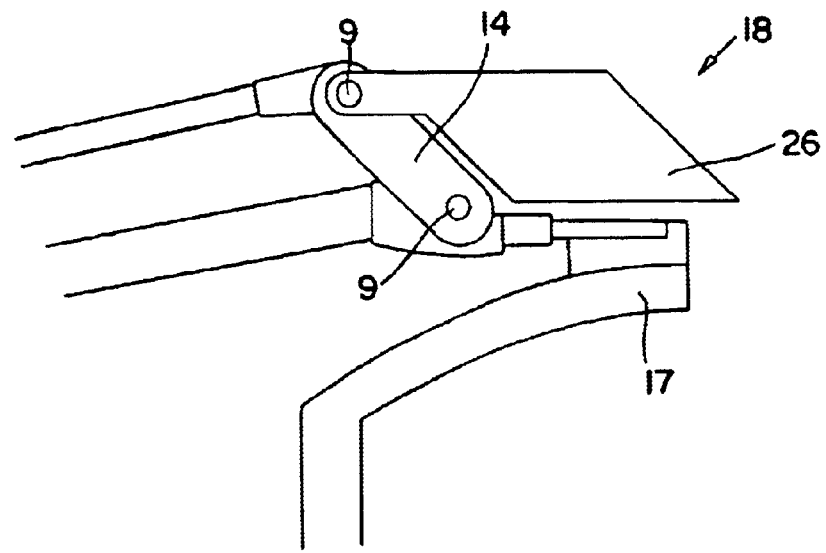
FIGS. 6a and 6b are details of the receiving device for accessory parts for the microscope.
Figure 6B:
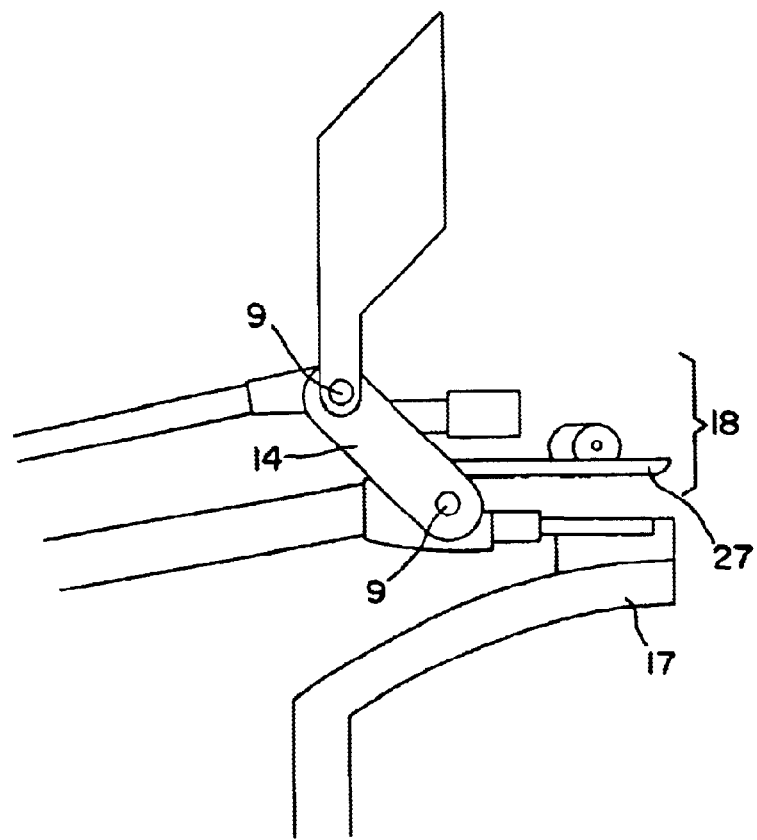

Details of the receiving device 18 are shown in FIGS. 6a and 6b. The receiving device in this embodiment comprises a tray 27 which is affixed to bar 14 and on which accessory parts can be placed. These parts can be received also by holders which e.g. are fixed to bar 14 as shown in FIG. 6b. the receiving device further comprises a cover 26 which is pivotably connected to hinge 9.

Receiving device 18 remains horizontally positioned. Pivot axles 4 and 16 are arranged under a fixed angle with respect to the horizontal, in the figure under 45. Because 5, 4, 16, 15, 9, 13, 9 is a parallelogram linkage, also part 13 will be arranged under 45 with respect to the horizontal. Because 13, 9, 12, 9, 14, 9, 8 is also a parallelogram linkage, part 14 will be always parallel to part 13 and thus also always oriented under 45 with respect to the horizontal. Therefore, device 18 is always horizontally aligned if as shown in FIG. 1 if it is aligned under 45 with respect to part 14.

The rotational moment (torque) which is exerted by the microscope 20, the receiving device 18 and the weights of the bars 8, 12, 13, 14 and the other parts of the first horizontal parallelogram linkage, can be perfectly compensated by the counterweight 10 If the bar 15 is held fixed. If rotation of the bar 5 about the pivot axle 4 is permitted, it is possible that the stand will fall into an extreme position. If the centre of gravity of the whole system is above the axle 4, the system stretches fully, and if it lies under the axle 4, the bar 5 moves until the angle a 90° is reached. By means of the further weight 11, the stand can now be compensated so that the centre of gravity lies in the pivot axle 4 and thus the microscope weight is compensated in each position irrespective of the angles α and β.

The weights 10 and 11 can be positioned at different places. Thus, the weight 10 can be secured at any point on the bar 6. The weight 10 can also be secured on the bar 7 or on the continuation thereof, in which case the weight 10 must then be made bigger or smaller to compensate the moments. The weight 11 can also be moved on the bar 7 or can be arranged on the bar 5 under the pivot axle 4 or on a downward continuation of the bar 5. In the latter case, a variation of the weight 11 is likewise necessary according to the distance from the pivot axle 4. The weights 10, 11 can also be combined partially or completely in one weight. The weights or parts thereof can also be arranged inside the bars 5, 6 or 7. In this way it is possible to keep the width of the stand as small as possible and to minimize the excursion of counterweights, by which means the theatre sister's access to the operating site is optimized.

On at least two hinges 9 of the stand, brakes are arranged which can be opened or closed by electrical actuation. One such brake 23, 24 is shown in FIG. 3. If the microscope 20 is to be spatially moved, all brakes are released by pressing a button on a hand piece of the operating microscope, as a result of which the microscope can be brought with minimal effort into any position inside the range of movement of the microscope 20. These brakes are preferably arranged in the hinge 9 in the compensating weight 10 and in the pivot axle 4, so that the weight of the brakes either has no influence or contributes to the weight compensation. The transformer for current supply is also preferably arranged at the hinge 9 at the weight 10.

The weights 10 and 11 are chosen such that, at a maximum weight of the operating microscope, the stand is fully compensated. The weights 10 and 11 are then fixed.

On the mounting device 17 for the microscope there is a receiving device 18, on or in which the accessory parts of the microscope can be arranged. This receiving device can either be a box or a holder with annular recesses similar to the fastening possibilities on the operating microscope, or a combination of the two. If, for example, the physician changes from a cranial operation, in which the assistant stands at the side of the operating surgeon, to a spinal column operation in which the assistant sits opposite the operating surgeon on the other side of the operating table, in order to prepare for the operation the theatre nurse only needs to remove the co-observation tube from the operating microscope and place it in the receiving device 18 on the mounting device 17 for the microscope. Conversely, she will remove a second viewing piece from the receiving device and will arrange it on the operating microscope 20 opposite the operating surgeon. In this way, the stand remains completely weight-compensated, without weights having to be moved or operating buttons having to be actuated. There is also no longer any need for the theatre nurse to carry an expensive optical element through the operating theatre or to a storage location and thus run the risk of the optical element being damaged.

If the overall configuration of the microscope has to be changed from time to time, for example by attachment of a lighter video camera, the stand has to be re-compensated only in these cases. This compensation should preferably be carried out by a service engineer or a hospital technician. To do this, weight elements are preferably either removed from or fitted on the compensating weights 10 and 11, or other weight elements are added or removed in the area of the mounting device 17 for the microscope or in the area of the receiving device 18. For this purpose, a set of weights is supplied with the operation system. In addition, the brake control is configured in such a way that the brakes in the pivot axle 4 and in the hinge 16 can be opened separately. For a technician, it is then a very simple matter to re-establish a perfect weight compensation with the new microscope weight.

For fine adjustment at the time of installation or after a subsequent change in the supporting weight, smaller weights can be arranged on the bars 5, 6 or 7, which smaller weights are moved and then fixed. It is also possible to design the weight 10 or 11 or both of them so that they are slightly movable, in order thereby to carry out fine adjustment.

Figure 4:
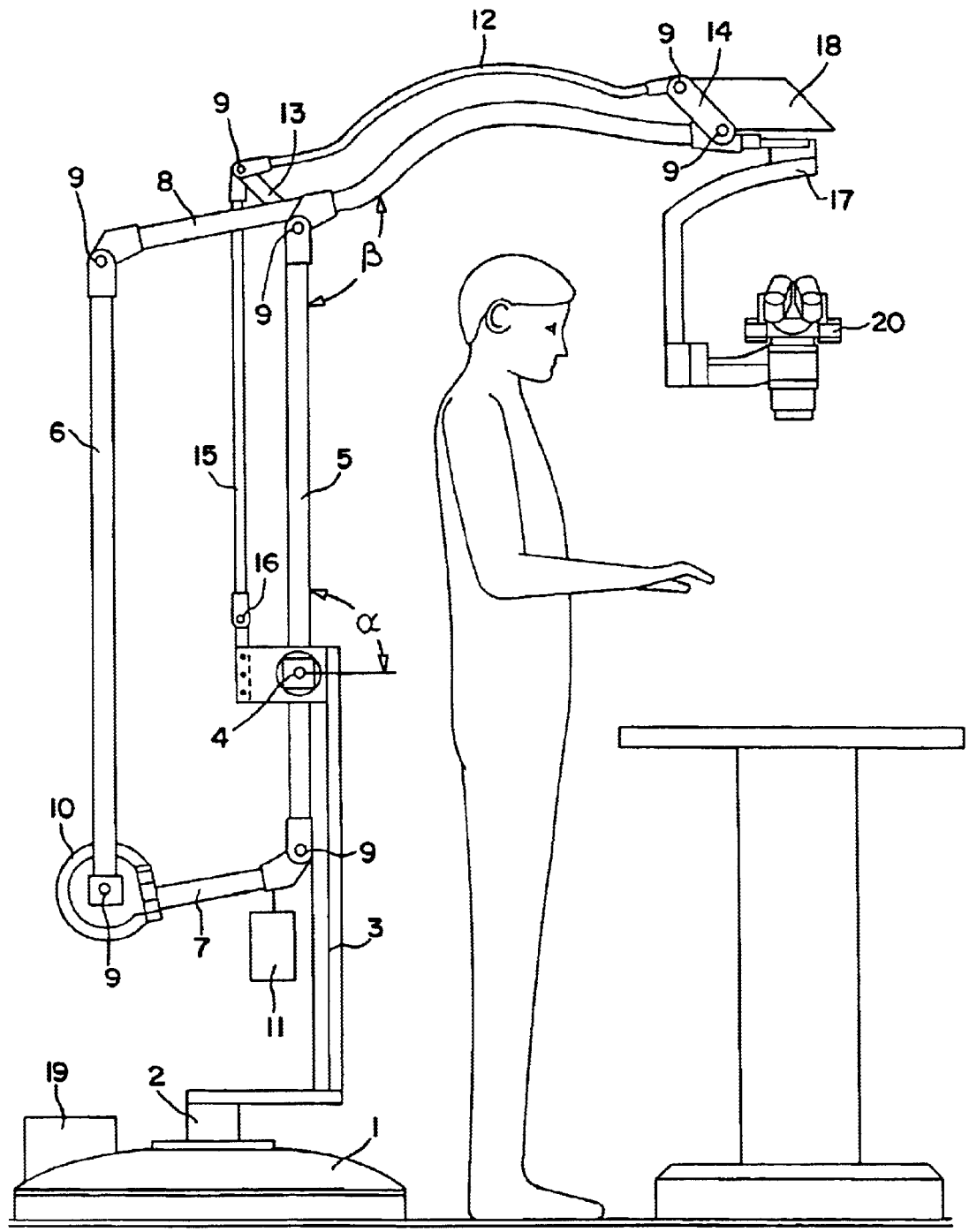
FIG. 4 is another embodiment of the microscope system according to the invention in a diagrammatic view from the side.

The bars 5, 6, 7, 8, 12, 13, 14, 15 are preferably designed as pipes, with different cross-sectional shapes being possible. The pipes can be connected to one another by bushings 21 (FIG. 3) in which the hinges for the movement are located. In this case, it is advantageous if the hinge axes are located outside the pipes. If in fact the pipe 8 is arranged above the hinges, height is gained for the surgeon when he is operating underneath the bars of the first parallelogram linkage. To gain still further height, it is also possible to provide the bar 8 with an upwardly directed curvature in the area in which the surgeon can stand during the operation. Such an embodiment is shown in FIG. 4.

As has already been described, the size of the receiving device 18 must be such as to be able to receive the accessory parts of the operating microscope 20. If many parts are to be changed from one operation to the next, it is also conceivable to accommodate these parts elsewhere, for example in a compartment 19 at the foot 1 of the stand, and, in their place, to remove different weights 1 from this compartment 19 and arrange them in the receiving device 18. Since these weights can have a much smaller volume, the receiving device 18 can turn out considerably smaller.

Where reference is made to bars of the parallelogram linkages, this means the parallelogram sides. One of these parallelogram sides between pivot axle 4 and hinge 16 is not of course such a bar or does not need to be such a bar. This is also the case for other so-called bars, in particular the bar 14. Instead of providing a bar 14, the bars 8 and 12 could be connected with hinges 9 directly to the receiving device 18.

What is claimed:

1. Microsurgical microscope system with a stand and with a microscope arranged thereon, in which system the stand has a base part and a substantially horizontal parallelogram linkage with two substantially horizontal bars and outer and inner further bars connecting the horizontal bars, of which the outer further bar is connected to a mounting device for the microscope, characterized in that the outer further bar also has a receiving device connected to it for accessory parts of the microscope, said mounting device, microscope, receiving device, and accessory parts having a total weight, said stand being balanced to support said total weight at said outer further bar and said total weight at said outer further bar remaining constant whether said accessory parts are attached to said microscope or located on said receiving device.

2. Microscope system according to claim 1, characterized in that a second receiving device for accessory parts of the microscope and additional weights is provided on the base part.

3. Microscope system according to claim 1, in which the parallelogram linkage forms a first parallelogram linkage, characterized in that the stand also has:

a second substantially vertical parallelogram linkage with two substantially vertical bars and two substantially horizontal bars, of which one of the substantially vertical bars is mounted on the base part so as to be able to pivot about a pivot axle, a third substantially vertical parallelogram linkage whose first lower hinge on the pivot axle of one of the substantially vertical bars of the second parallelogram linkage is connected to the base part, and whose second lower hinge is likewise connected to the base part and is connected via its upper bar to the first parallelogram linkage, where a substantially horizontal bar of the first parallelogram linkage is a continuation of the upper substantially horizontal bar of the second parallelogram linkage, where the second lower hinge of the third parallelogram linkage is arranged higher than the first, the connection line between first and second hinges forms with the horizontal an angle of approximately 30 to 60°, and the upper bar of the third parallelogram linkage forms the inner further bar of the first parallelogram linkage.

4. Microscope system according to claim 3, characterized in that the connection line between first and second hinges forms with the horizontal an angle of approximately 45°.

5. Microscope system according to claim 3, characterized in that electrically or pneumatically releasable brakes are arranged on hinges.

6. Microscope system according to claim 3, characterized in that it has weights which are arranged on the parallelogram linkages.

7. Microscope system according to claim 3, characterized in that the bars are pipes which are held in bushings which form parts of the hinges.

8. Microscope system according to claim 7, characterized in that the hinge axles are arranged in the bushings outside the longitudinal axis of the pipes.

9. Microscope system according to claim 3, characterized in that an electrically or pneumatically releasable brake is arranged on the pivot axle.

10. Microscope system according to claim 3, characterized in that it has weights which are arranged on the second parallelogram linkage.

11. Microscope system according to claim 3, characterized in that at least one bar is a pipe which is held in a bushing which forms a part of the pivot axle.

12. Microscope system according to claim 11, characterized in that the pivot axle is arranged in the bushing outside the longitudinal axis of the pipe.

13. Microscope system according to claim 1, characterized in that at least one bar of the parallelogram linkages is curved in the direction away from the operating site.

14. Microscope system according to claim 1, characterized in that the base part has a foot part and a column which is pivotable about a vertical axle.

15. Microscope system according to claim 1, comprising weights receivable on said receiving device to compensate for the weight of one or more of said accessory parts removed from said microscope and said receiving device.

* * * * *